United States Patent [19]

McRae

[11] Patent Number: Plant 5,949

[45] Date of Patent: Apr. 21, 1987

[54] ASIATIC LILY NAMED ROSEFIRE

[75] Inventor: Edward A. McRae, Boring, Oreg.

[73] Assignee: Melridge, Inc., Gresham, Oreg.

[21] Appl. No.: 710,428

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of hybrid Asiatic lily having large compact racemes of flowers of excellent form and large size, the flowers being particularly characterized by having a dramatic overall tri-colored pattern formed by a hexagonal arrangement of the tepals, each of which has its innermost part colored a bright orange-red bordered by a brilliant golden yellow flush and the remaining portion of each tepal being a bright fiery red. This color pattern is unique in the upright Asiatic division of lilies and the flowers have a long-lasting character, both on the plant and as cut flowers. The plant is an excellent garden plant, is highly resistant to disease, shows high tolerance to virus, and its bulbs may be precooled and forced for cut-flower production.

1 Drawing Figure

BACKGROUND OF THE NEW PLANT

My new variety of lily plant herein disclosed originated as a seedling selected from a group of seedlings resulting from my crossing an unnamed cultivar of *L.×hollandicum* (unpatented) and the cultivar "Connecticut King" (unpatented) at Sandy, Oreg., in the course of my breeding efforts carried on since the year 1971 with the object of producing superior upright-flowering Asiatic lilies having coloration of gold, orange, and red, suited to cut-flower production on a commercial scale.

This particular seedling was selected for propagation because of the large size and thick texture of its very broad tepals which collectively present a dramatic tri-colored bloom having a bright orange-red throat and a brilliant golden yellow central area, which is surrounded by a fiery red coloration which occupies about two-thirds of the total flower area. This selected seedling was asexually reproduced by me and under my direction at Sandy, Oreg., and successive generations produced by bulb-scale propagation and natural propagation from bulblets have demonstrated that this new lily plant has desirable characteristics of hybrid vigor, great hardiness, and a high degree of disease resistance, as well as all of the desirable characteristics of form, color, and habit. This generation to generation propagation has also shown that the plant is a vigorous and good grower and propagator, and that its clones force well for cut-flower production as observed at Sandy, Oreg., and that the novel and distinctive characteristics of this new variety hold true under asexual propagation from generation to generation and appear to be firmly fixed.

DESCRIPTION OF THE DRAWING

This new variety of lily plant is illustrated in the accompanying photographic drawing, which shows a face view of an open bloom, together with buds in various stages of growth, the view of the bloom illustrating the flower form and tepal arrangement, the unusually broad form of the tepals, and in particular, the novel and distinctive tri-colored pattern of the flower as a whole, the view being hand-painted to show the true coloration of the orange-red throat, golden yellow central portion, and the fiery red flower body whereby the tepals collectively in their hexagonal arrangement present a dramatic combination of contrasting colors.

DESCRIPTION OF THE NEW PLANT

The following is a detailed description of my new variety of Asiatic hybrid lily with color designations according to The R.H.S Colour Chart of The Royal Horticultural Society of London, England, and with nomenclature according to The International Lily Register, Second Edition, of The Royal Horticultural Society, the observations having been made of plants grown at Sandy, Oreg., since the summer and fall of 1984.

THE PLANT

Origin: Seedling.

Parentage:

*Seed parent.*—An old unnamed cultivar of *L.×hollandicum* (unpatented).

*Pollen parent.*—"Connecticut King" (unpatented).

Classification:

*Horticultural.*—Hybric lily cultivar, Division of I-A of the Horticultural Classification of Lilies by The Royal Horticultural Society.

*Commercial.*—Upright Asiatic hybrid lily.

Form: Single, erect, and stately.

Height: About 90 to 120 cm. from bulbs of about 12 to 15 cm. in circumference.

Growth: Vigorous and upright.

Foliage:

*Character.*—Sessile.

*Quantity.*—Abundant.

*Leaf size.*—About 8 to 12 cm. long and about 1.5 to 2 cm. wide at the base.

*Leaf shape.*—Lanceolate.

*Texture.*—Leathery.

*Aspect.*—Glossy.

*Color.*—Dark green.

Bulbs:

*Size.*—Ranging up to 25 cm. in circumference in commercial use.

*Color.*—White.

THE BUD

Form: Ovoid to long ovoid with obtuse ends.

Size: About 7 to 9 cm. long just prior to opening.

Opening rate: The bud opens slowly at maturity in response to light.

Color: Golden Yellow, RHS 12B, with base end and tips Orange Red, RHS 34B, when light levels are high, this color pattern being evident when the outer tepals first divide and when the tepals begin to unfurl.

Peduncle:

*Length.*—About 7 to 10 cm., depending upon light levels.

*Color.*—Green overlaid with plum.

THE FLOWER

Blooming habit: Annually, once and profusely, in early mid-season for Asiatic lilies. October-dug bulbs, properly precooled, planted under glass in western Oregon and with no supplementary lighting, flower in an average of 65 to 70 days when grown at moderate temperatures.

Size: Large; about 15 to 19 cm. in average.

Borne: As a compact raceme of about 6 to 12 buds and flowers on a single stem.

Shape: Flat to slightly dish-shaped with recurved tepal tips.

Tepalage:

*Number.*—Six.

*Arrangement.*—Hexagonal with petals angulated about sixty degrees relative to the sepals.

*Shape.*—Elliptic with unusually broad midsection, entire margins, and acute tip.

*Texture.*—Thick.

*Color.*—The innermost part of each of the tepals, at its base, is a bright Orange Red, RHS 34A, and extending beyond this area, there is a Yellow Golden flush, RHS 12A, about 2 to 3 cm. wide and 2 to 3 cm. long, the remainder of each of the tepals being a bright fiery Red, RHS 34 A-B. The deeper red area may fade as the flower matures to a more bronzed or lighter Red, RHS 31 A-B, especially if the flowers are subjected to very high temperatures and bright light.

*Spotting.*—There is very inconspicuous spotting, a few tiny spots appearing parallel with the nectary.

*Color change.*—The flower may become lighter Orange Red, RHS 31 A-B or a more bronze red as the flower ages, especially if the flowers are subjected to high temperatures and bright light.

*Tepal longevity.*—The tepals stay on the stem for about three weeks.

Fragrance: None.

Disease resistance: The flower and plant are resistant to disease, and in particular, they are resistant to Fusarium and Botrytis.

Lasting quality: The flower is long lasting, both on the plant and as a cut flower.

REPRODUCTIVE ORGANS

Stamens:

*Number.*—Six.

*Arrangement.*—Typical of genus Lilium.

Anthers:

*Color.*—Greyed Gold, RHS 167A.

Filaments:

*Length.*—About 5 cm.

*Color.*—Orange Red, RHS 31 A-B.

Pollen color: Greyed Gold, RHS 167A.

Pistils:

*Number.*—One.

Style:

*Length.*—About 5 cm.

Stigma:

*Color.*—Soft orange red with light plum overlay.

Ovary: Typical of genus Lilium.

THE FRUIT

Fertility: The fruit is fertile.

Shape: Ovoid.

Color at maturity: Soft brown, sometimes overlaid with light plum.

This new variety of Asiatic lily most nearly resembles the species *Lilium bulbiferum* but has larger flowers and a more intense color pattern, with virtually no spots, and a higher bud count with improved inflorescence. Also, it does not show the virus susceptibility or the inability of the species to adapt to acid soils.

I claim:

1. A new and distinct variety of Asiatic hybrid lily, substantially as herein shown and described, characterized in particular by the excellence of its flower form and substance and its dramatic tri-colored pattern of orange red throat, a golden central flush, and a fiery red body beyond the central flush area.

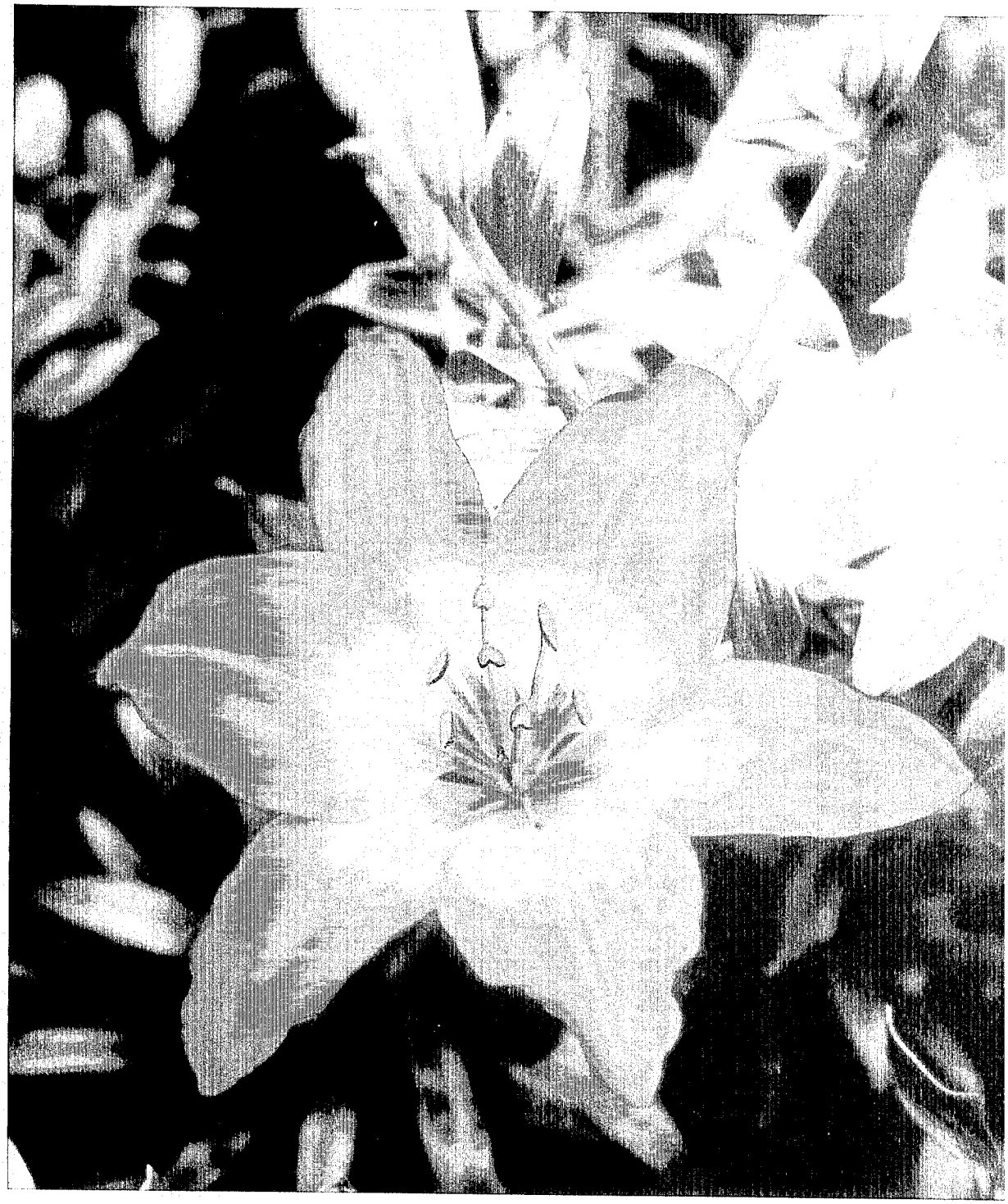

* * * * *